US00RE33854E

United States Patent [19]

Adair

[11] E Patent Number: Re. 33,854

[45] Reissued Date of Patent: Mar. 24, 1992

[54] RIGID VIDEO ENDOSCOPE WITH [HEAT] STERILIZABLE SHEATH

[76] Inventor: Edwin L. Adair, 99 Inverness Dr. East, Englewood, Colo. 80112

[21] Appl. No.: 597,499

[22] Filed: Oct. 15, 1990

Related U.S. Patent Documents

Reissue of:

[64] Patent No.: 4,878,485
Issued: Nov. 7, 1989
Appl. No.: 306,815
Filed: Feb. 3, 1989

[51] Int. Cl.[5] ..... A61B 1/00

[52] U.S. Cl. ..... 128/6; 128/4; 604/263

[58] Field of Search ..... 128/6, 4; 604/280, 263

[56] References Cited

U.S. PATENT DOCUMENTS

| | | | |
|---|---|---|---|
| 3,794,091 | 2/1974 | Ersek et al. | 128/23 X |
| 3,809,072 | 5/1974 | Ersek et al. | 128/23 |
| 3,866,601 | 2/1975 | Russell | 128/4 |
| 4,132,227 | 1/1979 | Ibe | 128/4 |
| 4,201,199 | 5/1980 | Smith | 128/7 |
| 4,254,762 | 3/1981 | Yoon | 128/4 |
| 4,327,735 | 5/1982 | Hampson | 604/171 |
| 4,646,722 | 3/1987 | Silverstein et al. | 128/4 |
| 4,721,097 | 1/1988 | D'Amelio | 128/4 |
| 4,741,326 | 5/1988 | Sidall et al. | 128/4 |
| 4,772,275 | 9/1988 | Erlich | 604/280 |

FOREIGN PATENT DOCUMENTS 1405025 9/1975 United Kingdom .

*Primary Examiner*—William H. Grieb
*Attorney, Agent, or Firm*—Fields, Lewis, Pittenger & Rost

[57] ABSTRACT

A video endoscope is provided which has an inner cylindrical body member containing the optics and electronics in a manner which is impervious to liquid so that the inner member can be soaked in a disinfectant between uses. An outer rigid cylindrical sheath is provided into which the inner member is inserted during an operation. This outer sheath is [heat] sterilizable and therefore is in a sterile condition at the time of use. The inner body releasably locks into the outer sheath. The outer sheath also includes an accordion shaped sleeve at the proximate end which can be drawn down around the trailing cables containing the optics and electronics so that the entire endoscope is sterile for use within the operating room. After use, the inner body member can be removed and the outer sheath can be disposed of or it can be resterilized by heat for use at a subsequent time. Any containments from the body of the patient will be removed with the outer sheath and kept completely separated from the inner body member so that there can be no transmittal of containments from the body of one patient to that of a subsequent patient.

13 Claims, 2 Drawing Sheets

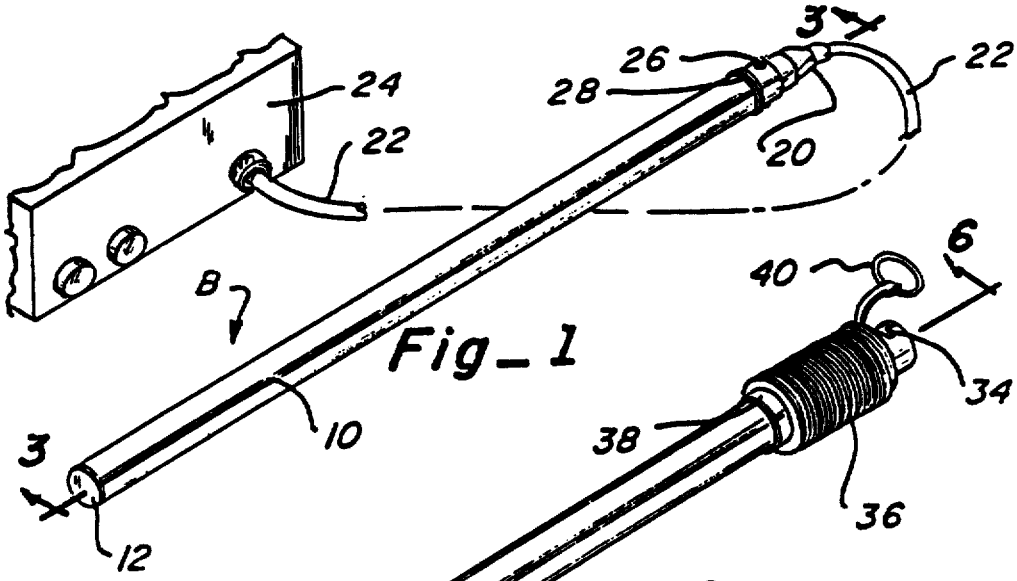
Fig_1
Fig_2
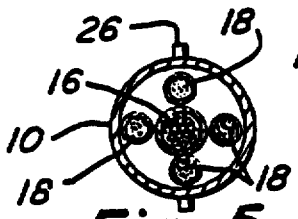
Fig_5
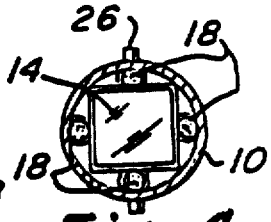
Fig_4
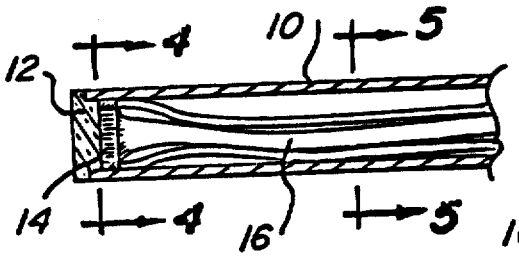
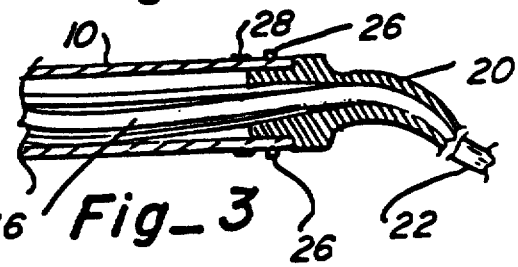
Fig_3
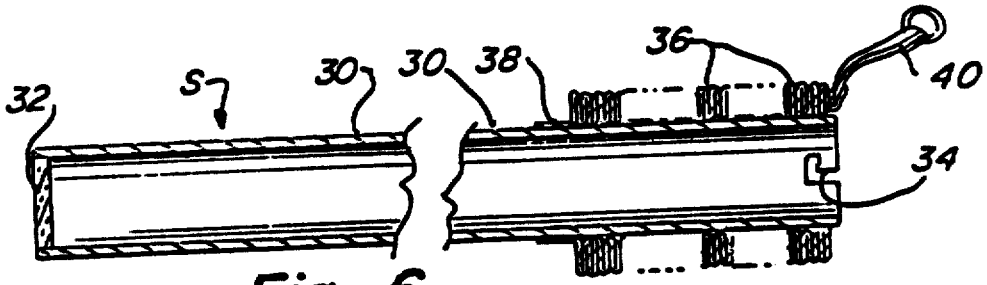
Fig_6
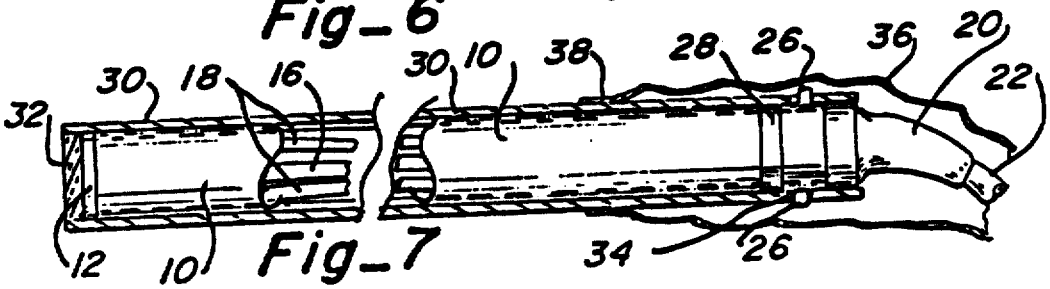
Fig_7

RIGID VIDEO ENDOSCOPE WITH [HEAT] STERILIZABLE SHEATH

Matter enclosed in heavy brackets [ ] appears in the original patent but forms no part of this reissue specification; matter printed in italics indicates the additions made by reissue.

TECHNICAL FIELD

This invention relates to a video endoscope and more particularly to such an endoscope having a moisture tight inner cylindrical body containing electronics and optics which can be disinfected by soaking and an outer rigid sterilizable sheath for containing and covering the inner body during an operation, the outer sheath being sterilized by heat and having a sterilizable sleeve for extending over the trailing cable containing the electronic and optic fibers.

BACKGROUND ART

Over the years many developments have been made in the endoscope art. Particularly, these developments have been attempts to provide endoscopes which will serve a variety of functions and which are maintained in a sterile condition during use.

Ersek et al. U.S. Pat. Nos. 3,794,091 and 3,809,072 each disclose a flexible sheath which is sterile at the time of manufacture and can be rolled up onto an endoscope to provide sterility. However, there is no seal at the proximate end of the sheath and therefore bacteria can enter between the endoscope and sheath and there is no provision for maintaining the distal end of the endoscope in a sterile or protected condition.

Russel U.S. Pat. No. 3,866,601 discloses a speculum in which a penetrating tube slidably receives a guide tube and is surrounded by a flexible sheath.

Ibe U.S. Pat. No. 4,132,227 discloses an endoscope surrounded by a hollow cylindrical sheath extending toward but not to the distal end of the endoscope in order to create a fluid channel in the space between the sheath and the endoscope.

Smith U.S. Pat. No. 4,201,199 discloses an endoscope surrounded by a rigid glass or plastic tube having an enlarged bulb at its distal end to space tissue away from the viewing window of the endoscope. The window is formed at an angle to provide viewing of a site offset from the axis of the endoscope.

Yoon U.S. Pat. No. 4,254,762 discloses an endoscope surrounded by a sheath having a transparent lens at its distal end. The sheath may be at least partially open at its distal end for use with endoscopes having biopsy channels.

Hampson U.S. Pat. No. 4,327,735 discloses a catheter surrounded by a transparent, collapsible sleeve through which the catheter projects at its distal end.

Silverstein et al. U.S. Pat. No. 4,646,722 discloses another endoscope having a sterile flexible sheath which can be rolled up along the endoscope. A channel is provided between the endoscope and sheath through which biopsies can be taken. The sheath is not sealed at the upper end and will not maintain the sterility which is required within an operating room.

D'Amelio U.S. Pat. No. 4,721,097 discloses another flexible sheath for use on an endoscope which has no seal at the upper end and does not provide the sterility required in an operating room.

Sidall et al. U.S. Pat. No. 4,741,326 discloses a further flexible sheath which is rolled up along the endoscope and does not provide sterility or protection of the entire endoscopic device.

Brown British Patent No. 1,405,025 discloses a proctoscope surrounded by a concentric tube for providing a fluid channel.

DISCLOSURE OF THE INVENTION

In accordance with the present invention, a rigid video endoscope is provided which comprises an inner cylindrical body member having a distal end and a proximate end. A light transmitting element is sealed to the distal end of the body member. An image sensor is mounted against the light transmitting element within the body member. An electronic cable within the body member has a distal end connected to the image sensor and a proximate end extending beyond the proximate end of the body member and connectable to a video control unit. At least one fiber optic bundle for light transmission is provided within the body member and has a distal end adjacent the light transmitting element and a proximate end extending beyond the proximate end of the body member and connectable to a xenon, halogen or incandescent light source. A strain relief fixture is sealingly attached to the proximate end of the body member with the electronic cable and jacketed fiber optic bundle extending therethrough and sealed to the fixture. An outer rigid cylindrical heat sterilizable sheath, having a distal end and a proximate end, is provided for receiving the inner body member and is of substantially the same length as the body member. A window is sealed to the distal end of the sheath. An accordion-folded, heat sterilizable, cylindrical sleeve is mounted adjacent the proximate end of the sheath and is extendable along the electronic cable and the optical bundle for a substantial distance to maintain sterility of the video endoscope within the sterile field of the operating room. Means is provided for releasably locking the body member within the sheath.

A tab can be provided on the sleeve for extending it along the electronic cable and fiber optic bundle. A releasable locking means can include a bayonet slot at the proximate end of the sheath and a pin at the proximate end of the body member which is releasably engageable with the bayonet slot. If desired, the window can be a prism for viewing at an angle to the longitudinal axis of the endoscope.

In one embodiment the body member is concentrically aligned with the sheath. In another embodiment the body member is eccentrically mounted within the sheath. In this later arrangement the window has apertures therein and channels within the sheath corresponding in number to the apertures to provide access to the site under investigation. These channels can be used for providing gas or a steerable device can be inserted through one of them to carry out a procedure, such as taking a biopsy at the site. It also could provide a channel for a laser fiber. The body member may be backed filled with nitrogen under pressure to minimize the possibility of any liquids entering into that device.

With this arrangement, the inner cylindrical body member contains all of the optics and electronics and can be disinfected by soaking it in a disinfecting solution. However, disinfecting is not sterilization and therefore is generally not acceptable for use within the operating room. It particularly is not acceptable in open surgical procedures and in orthopedic surgery and neurosurgery. Thus, the rigid sterilizable sheath on the exterior can be properly sterilized by heat treatment and then slipped over the inner cylindrical body. The accordion-folded sleeve on the sheath can be extended along the optical bundle and electronic cable for a sufficient distance to provide a sterile barrier between them and the operating site. This outer sheath can be made of disposable material or it can be resterilized for subsequent usage. Thus, all portions of the device which come in contact with the patient can be sterilized even though the associated electronics and optics cannot be sterilized. After use, any contaminates from the patient's body will be removed with the outer sheath and not contact the inner body member. Thus, the contamination cannot to transmitted to the next patient since the body member will be inserted in another sterile sheath.

The term "light transmitting element" as used herein is intended to include any type of light transmitting device which may have any one or several optical qualities. For example, it may simply be a transparent panel made of glass, plastic or sapphire. On the other hand, it may comprise one or more lenses for magnification or to increase the field of view. It can include a series of adjustable lenses to provide variable magnification and serve as a microscope.

Additional advantages of this invention will become apparent from the description follows, taken in conjunction with the accompanying drawings.

BRIEF DESCRIPTION OF THE DRAWINGS

FIG. 1 is a perspective view of the inner cylindrical body member which forms a part of the video endoscope of this invention;

FIG. 2 is a perspective view of the outer cylindrical heat sterilizable sheath which forms the other part of the video endoscope of this invention;

FIG. 3 is a condensed, longitudinal section, taken along line 3—3 of FIG. 1, showing the internal details of the cylindrical body member;

FIG. 4 is an enlarged vertical section, taken along line 4—4 of FIG. 3, showing the arrangement of the image sensor and optical fiber bundles;

FIG. 5 is an enlarged vertical section, taken along line 5—5 of FIG. 3, showing the position of the electronic cable and the fiber optic bundles within the body member;

FIG. 6 is a condensed longitudinal section, taken along line 6—6 of the FIG. 2, showing further details of the heat sterilizable sheath;

FIG. 7 is a condensed longitudinal section, showing the cylindrical body member positioned within the heat sterilizable sheath;

BEST MODE FOR CARRYING OUT THE INVENTION

Figure 9:
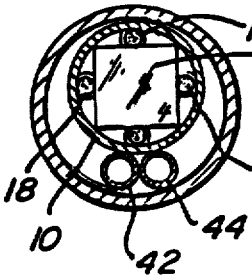
FIG. 9 is an enlarged vertical section, taken along line 9—9 of FIG. 8, showing the arrangement of the body member within the sheath and the positioning of the gas channels.
Figure 8:
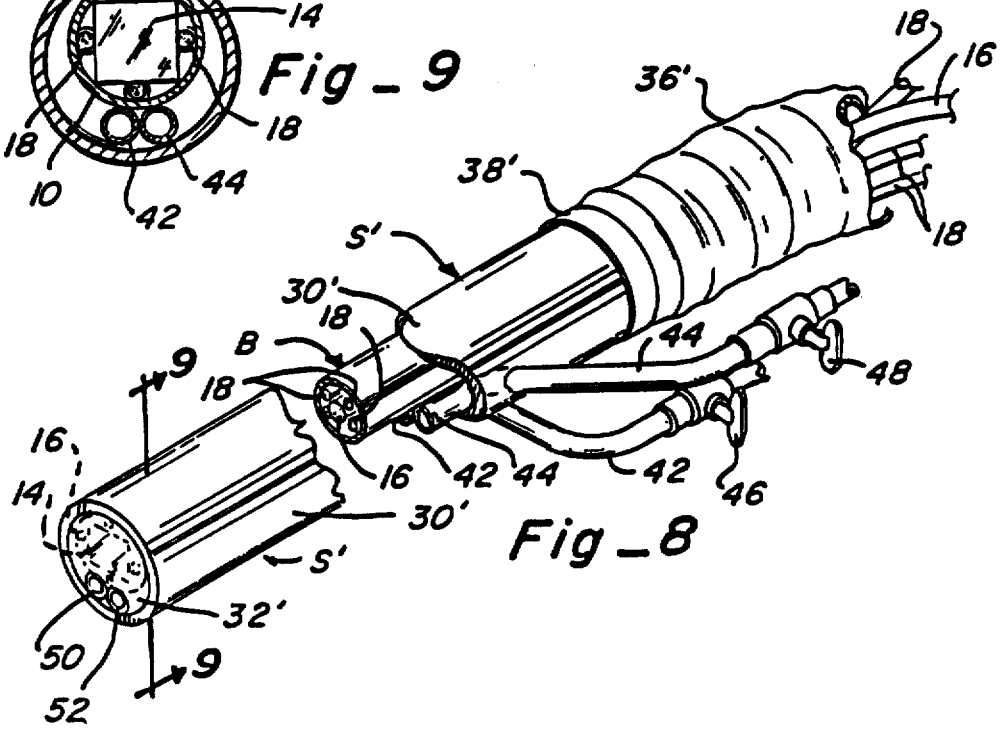
FIG. 8 is a fragmentary perspective view of an alternative video endoscope.

In accordance with this invention a video endoscope is provided which has an inner body member B, shown in FIGS. 1 and 3, for containing the optics and electronics for the endoscope and an outer rigid, [heat] sterilizable sheath S for receiving the body member and providing a sterile outer casing for coming in contact with the patient and for extending over the connecting cables to provide a sterile environment for the operative procedure on the patient.

The inner body member M has a cylindrical housing 10 provided at its distal end with a light transmitting device 12 which is sealably attached thereto to minimize the possibility of any fluids entering at this location. An image sensor 14, such as a CCD is mounted on the inside of light transmitting device 12 for receiving light transmitted through the window at the investigative site, such as within a body cavity. The image sensor also may be a CCD, CID, CPD or [MDS] *MOS* device, depending upon application. This CCD may be on the order of 1.0 mm×1.0 mm. A typical laproscope is 0.8 cm to 1.2 cm in diameter and would utilize a correspondingly larger CCD device, a typical arthroscope is 4.0 mm in diameter and would utilize a much smaller CCD sensor. The window may include optics to focus an image on the CCD and provide a focal length of 0.5 cm to 15 cm, depending on the intended use of the endoscope. Field of view may be altered by the use of different lenses and may range from 15° to 140° or more. An electronic cable 16 has a distal end connected to the image sensor 14 and runs longitudinally through housing 10, as shown in FIG. 3.

Conveniently, optical fiber bundles 18 have distal ends positioned adjacent light transmitting element 12 and spaced around image sensor 14. The exact number of optical fiber bundles and type of fiber will depend upon the particular usage of the endoscope. Four such optical fiber bundles have been shown in the drawings, one being positioned on each of the four sides of image sensor 14. However, a greater or smaller number could be provided, as required. The number of optical fiber bundles may be optimized to allow transmission of various light frequencies, including laser light. These optical fiber bundles 18 also run through housing 10 and pass through a strain relief fixture 20 which seals the proximate end of housing 10. This fixture is also sealed around these cables and extend beyond the fixture through the center of a connecting cable 22 whose opposite end is connected to a video processing unit 24 having a suitable viewing screen (not shown) and light sources (not shown) as required and as is apparent to one skilled in the art. The cylindrical housing is completely sealed against the entry of moisture by window 12 and fixture 20. It also may be backfilled with nitrogen gas under pressure to help keep moisture out. After each use, it can be soaked in a disinfectant, such as gluleraldehyde or Chlorox.

Conveniently, the distal end of housing 10 is provided with oppositely extending pins 26 for connection to a bayonet slot on sheath 5 as described below. Also, an O-ring 28 is provided for forming a seal with outer sheath S, as described below. The seal could also be a threaded seal, with a threaded collar on the outer unit fitting into a threaded collar in the inner unit.

Sheath S comprises a cylindrical housing 30 which has a window 32 at its distal end and a bayonet slot 34 at its proximate end for cooperating with pins 26 to lock inner body member B within outer sheath S. Advantageously, an accordion-folded sleeve 36 is provided adjacent the proximate end of housing 30 and has a flange 38 attached to housing 30, as by adhesive and includes a pull tab 40 for extending the sleeve over strain relief fixture 20 and connecting cable 22 as best seen FIG. 7. These parts can be made of Teflon or other materials which can withstand high sterilization temperatures. The window can be made of glass or sapphire or polycarbonate which can stand the sterilization heat or other materials which are clear and withstand high temperatures of heat sterilization.

Referring to FIG. 7, it can be seen that when the endoscope is ready for use, the inner body member is locked within outer sheath S and light transmitting element 14 thereof is adjacent window 32 of the sheath. Thus, the inner body member is completely encased in the sterile outer sheath. Furthermore, the sterile sleeve 36 extends over the strain relief fixture and connecting cable to provide a completely sterile endoscope in the operating room and particularly at the site at which the operation or medical procedure is being conducted.

After use, the inner body member can be removed from the outer sheath S and sleeve 36 by twisting it slightly to release pins 26 from bayonet slot 34 whereupon it can be withdrawn. The outer sheath and sleeve 36 can be thrown away or it can be heated to a sufficient temperature and pressure for sterilization.

Also, it will be apparent that any contamination from the body of the patient which may repose on the outer sheath or the sleeve will be stripped away from the inner body member along with the outer sheath and therefore not be transmitted to the body member. The inner body member can then be soaked in a disinfectant and reinserted in another sterile outer sheath and sleeve for use on a subsequent operation. Obviously, a supply of the relatively inexpensive outer sheath and sleeve assemblies can be maintained so that the inner body member can be quickly made ready for a subsequent operation. The video endoscope of this invention can be used as a laparoscope, cystoscope, arthroscope, and for pelviscopy. With suitable optics, it could be used as a sterile operating microscope.

An alternative embodiment is shown in FIGS. 8–11 wherein a larger outer sheath S' is provided around inner body member B. This sheath S' has a cylindrical housing 30, with a lens 32, at the distal end and a sleeve 36, at the proximate end attached by means of a flange 38, The additional space is occupied by one or more tubes or channels, such as tubes 42 and 44 for supplying gas or fluids to the site under investigation. Conveniently, these tubes have control valves 46 and 48 respectively for controlling the flow of the gases and to prevent gas leakage during a procedure. The gas can be carbon dioxide which may be provided for the purpose of clearing and distending the site under investigation for better viewing. Also, a vacuum could be applied through one of the channels for aspiration of unwanted material from the viewing site. Conveniently, the distal ends of these tubes are connected to apertures 50 and 52, respectively in window 32'. These channels or tubes can be used for insertion of laser fibers, biopsy devices, grasping devices, etc.

Figure 10:
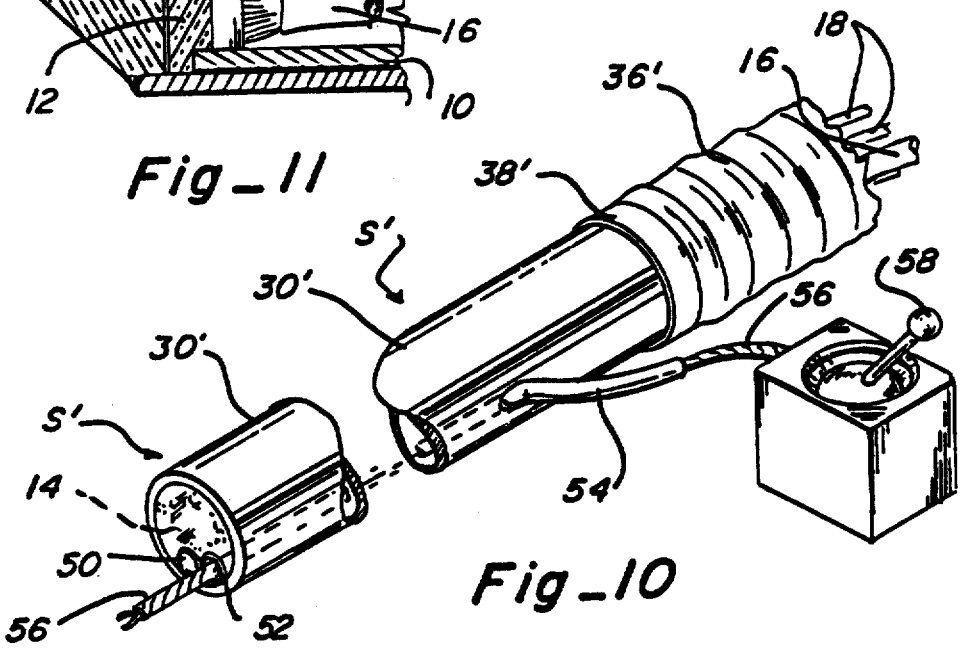
FIG. 10 is a fragmentary perspective view, similar to FIG. 8, but showing a passageway for use with a steerable device.

In FIG. 10 the same device is shown for use with a steerable device. In this case, a channel or tube 54 is provided which enters through housing wall 30' and extends longitudinally therealong and through aperture 52. Within this tube 54 is a steerable device, such as a biopsy sampling device 56 which is operated by a joy stick 58, as shown.

Figure 11:
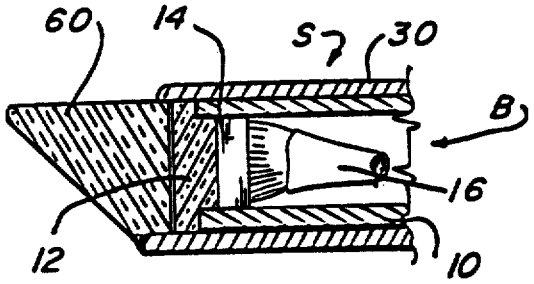
FIG. 11 is a fragmentary section of an alternative construction wherein the window of the sheath is in the form of a prism.

Finally, a further alternative embodiment is shown in FIG. 11 wherein the outer sheath S is provided with a prism 60 in place of the front window 32 so that the device can be used to view at any suitable angle to the longitudinal axis of the endoscope. The image sensor may be placed at various angles to the longitudinal axis of the tubular housing, for instance at 30°, 45°, or 90°. In this variation, the window in the [heat ] sterilizable sheath would be placed at a corresponding angle to match the orientation of the sensor.

From the foregoing, the advantages of this invention are readily apparent. An endoscope has been provided which is formed in two parts, an inner body member and an outer sheath. The inner body member contains all of the optics and electronics and is sealed against moisture so that it can be soaked in a disinfectant between usages. However, in most situations such disinfecting is not sufficient for safe subsequent use in the operating room. Therefore, an outer sheath is provided which can be heat sterilized prior to use and can be slipped over the inner body member and releasably locked thereto to provide an outer sterile covering. The outer sheath includes an accordion shaped sleeve at the proximate end which can be extended over the trailing cables of the inner member which contain the optical fibers and electronic cables to provide a sterile covering so that the device can be used in the operating room at the operating site. After use, the inner body member can be removed from the outer sheath and the sheath can either be thrown away or resterilized. Also, any contamination from the body of the patient will be removed with the outer sheath and will not come in contact with the inner body member, thereby minimizing any transmittal of disease from one patient to the next.

This invention has been described in detail with reference to particular embodiments thereof, but it will be understood that various other modifications can be effected within the spirit and scope of this invention.

I claim:

1. A rigid video endoscope comprising:

an inner cylindrical body member having a distal end and a proximate end;

a light transmitting element sealed to said distal end of said body member;

an image sensor mounted against said element within said body member;

an electronic cable within said body member, having a distal end connected to said image sensor and a proximate end extending beyond said proximate end of said body member and connectable to a video processing unit;

at least one fiber optic bundle within said body member, having a distal end adjacent said element and a proximate end extending beyond said proximate end of said body member and connectable to the video processing unit;

a strain relief fixture sealingly attached to said proximate end of said body member, said electronic cable and said fiber optic bundle extending through said fixture, said fixture being sealed thereto;

an outer cylindrical [heat] sterilizable sheath, having a distal end and a proximate end, for receiving said inner body member and being of substantially the same length as said body member;

a window sealed to said distal end of said sleeve;

an accordion-folded, [heat] sterilizable, cylindrical sleeve mounted adjacent said proximate end of said sheath and extendable along said electronic cable and said optical bundle for a substantial distance for maintaining sterility of said video endoscope within an operating room; and means for releasably locking said body member within said sheath.

2. Apparatus, as claimed in claim 1, further including:

a tab on said sleeve for extending it along said electronic cable and said fiber optic bundle.

3. Apparatus, as claimed in claim 1, wherein said releasable locking means includes:

a bayonet slot at said proximate end of said sheath; and a pin at said proximate end of said body member which is releasably engageable with said bayonet *slot*.

4. Apparatus, as claimed in claim 1, wherein:

said window is a prism for viewing at an angle to the longitudinal axis of said endoscope.

5. Apparatus, as claimed in claim 1, wherein:

said light transmitting means includes optics for magnifying an image.

6. Apparatus, as claimed in claim 1, wherein:

said light transmitting means includes optics for changing the field of view.

7. Apparatus, as claimed in claim 1, wherein:

said body member is concentrically aligned within said sheath.

8. Apparatus, as claimed in claim 1, wherein:

said body member is eccentrically mounted within said sheath.

9. Apparatus, as claimed in claim 8, further including:

means defining at least one aperture in said window; and at least one channel within said sheath between said sheath and said body member and having a distal end communicating with said aperture to provide access to a site under investigation.

10. Apparatus, as claimed in claim 9, wherein:

said aperture defining means defines a plurality of apertures;

a plurality of channels are provided within said sheath[is] *; each* having a distal end communicating respectively with one of said apertures;

means supplying a gas through at least one of said channels; and valve means connected to a proximate portion of said one channel to control the flow of gas.

11. Apparatus, as claimed in claim 1, wherein:

a steerable device is inserted through one of said other channels for carrying out a procedure at the site under investigation.

12. Apparatus, as claimed in claim 1, wherein:

said body member is backfilled with nitrogen under pressure.

13. A [heat] sterilizable sheath for an endoscope having a cylindrical body portion which contains within it an image sensor, an electronic cable connected to the sensor and at least one optical fiber bundle, said sheath comprising:

a cylindrical housing, having a distal end and a proximate end, for receiving the body portion of said endoscope;

a light transmitting element sealed to said distal end of said sleeve for transmitting a light image of the site under investigation to the image sensor;

an accordion-folded, [heat] sterilizable, cylindrical sleeve mounted adjacent said proximate end of said sheath and extendable along said electronic cable and said optical bundle for a substantial distance to maintain sterility of said endoscope within an operating room; and means for releasably locking said distal ends of said body and said housing together.

* * * * *